(12) United States Patent
Huang et al.

(10) Patent No.: US 7,266,461 B2
(45) Date of Patent: Sep. 4, 2007

(54) METHODS FOR ADJUSTING STRESS WAVE VELOCITY-BASED PREDICTIONS OF LUMBER STIFFNESS AND WARP PROPENSITY OF A TIMBER-BASED RAW MATERIAL GROUP

(75) Inventors: Chih-Lin Huang, Bellevue, WA (US); Stanley L. Floyd, Enumclaw, WA (US)

(73) Assignee: Weyerhaeuser Co., Federal Way, WA (US)

( * ) Notice: Subject to any disclaimer, the term of this patent is extended or adjusted under 35 U.S.C. 154(b) by 0 days.

(21) Appl. No.: 11/312,191

(22) Filed: Dec. 19, 2005

(65) Prior Publication Data

US 2007/0156353 A1 Jul. 5, 2007

(51) Int. Cl.
*G01L 1/00* (2006.01)
(52) U.S. Cl. .............................. 702/42; 73/781; 73/801
(58) Field of Classification Search .................. 702/33, 702/35, 39, 41, 42, 56, 85, 103, 105, 157; 73/574, 575, 760, 781, 801, 826, 12.01, 12.09, 73/788; 209/517–521; 144/356, 357, 382
See application file for complete search history.

(56) References Cited

U.S. PATENT DOCUMENTS

| | | | |
|---|---|---|---|
| 6,305,224 B1 * | 10/2001 | Stanish et al. ................. 73/597 |
| 6,308,571 B1 * | 10/2001 | Stanish et al. ................. 73/597 |
| 6,598,477 B2 * | 7/2003 | Floyd ............................. 73/597 |
| 6,715,337 B2 * | 4/2004 | Huang et al. ................. 73/12.12 |
| 6,889,551 B2 * | 5/2005 | Andrews et al. ............... 73/597 |
| 2003/0079544 A1 | 5/2003 | Floyd |
| 2006/0185441 A1 * | 8/2006 | Wang et al. .................... 73/801 |

OTHER PUBLICATIONS

Huang CL, "Predicting lumber, stiffness of standing trees," Proceedings of the 12th International Symposium on Nondestructive Testing of Wood University of Western Hungary, Sopron, Sep. 13-15, 2000, ISBN 963 7180 88 5.

Wang X "Acoustic analysis of warp potential of green ponderosa pine," Proceedings, 9th International IUFRO Wood Drying Conf, Aug. 25, 2005, pp. 155-160.

* cited by examiner

*Primary Examiner*—Eliseo Ramos-Feliciano
*Assistant Examiner*—Manuel L Barbee

(57) ABSTRACT

Methods are provided for predicting properties based on stress wave velocity measurements, such as modulus of elasticity (MOE) and/or warp potential of trees and/or logs from a timber-based raw material group ("TBRMG"). The methods provide a formula allowing compensation for growth rate differences between stands. Accordingly, the present invention prevents underestimation or overestimation of MOE and/or warp potential.

18 Claims, 6 Drawing Sheets

Cross Section of Log Having High Percentage of Mature Wood

Low SWV

Lumber with Low Juvenile Wood %

Cross Section of Log Having Low Percentage of Mature Wood

High SWV

Lumber with High Juvenile Wood %

FIGURE 3
Dierks study, 1996

| Stand | Log Diameter (inch) | Thinning Diameter | Juvenile wood % | SWV (m/s) | lumber MOE (10^6 psi) | Crook (inch) |
|---|---|---|---|---|---|---|
| 7 | 14.4 | 9.8 | 46 | 3627 | 1.218 | 0.373 |
| m | 14.4 | 7.2 | 25 | 3203 | 1.199 | 0.317 |
| c | 14.2 | 8.5 | 36 | 3311 | 1.157 | 0.375 |
| a | 14.1 | 10.2 | 52 | 3531 | 1.144 | 0.421 |
| j | 14.6 | 10 | 47 | 2781 | 0.934 | 0.408 |
| average | 14.34 | 9.14 | 41.28 | 3291 | 1.1304 | 0.379 |

METHODS FOR ADJUSTING STRESS WAVE VELOCITY-BASED PREDICTIONS OF LUMBER STIFFNESS AND WARP PROPENSITY OF A TIMBER-BASED RAW MATERIAL GROUP

FIELD OF THE INVENTION

This invention relates generally to a method for adjusting stress wave velocity based predictions of wood product properties to compensate for growth rate differences.

BACKGROUND OF THE INVENTION

It is generally known that acoustic measurement can be used to determine properties of a wood product, such as a log, tree, board, or the like. These properties may include, for example, stiffness, strength, shrinkage, and other characteristics. In some embodiments, in which properties of a wood product are being ascertained, a stress wave is induced into the wood product. Next, a measurement is taken with respect to the time in which the stress wave travels from a first end to a second end of the wood product. From this time interval, a velocity of the stress wave can be determined via the equation:

$$v = d/t$$

Where "v" is velocity of the stress wave; "d" is the distance traveled by the stress wave; and "t" is the time period of travel. This method of determining velocity is commonly referred to as a "time-of-flight" method. The velocity can, for example, be correlated to a modulus of elasticity ("MOE") for the wood product, which is an indicator of the stiffness of the wood product. The velocity can also be correlated to warp potential for the wood product.

These types of measurements are most commonly taken on the outer wood, or mature wood, of a standing tree to assess stiffness and warp propensity of the lumber converted from a pre-harvest forest stand. Trees and stands demonstrating high values for stress wave velocity ("SWV") generally will produce lumber that is stiff and stable, as well as less prone to warp.

Juvenile wood, or wood comprising approximately the first 10-15 growth rings has low stiffness, has a steep shrinkage gradient, and is more prone to warp than mature wood. As a result, the outer wood measurement of stress wave velocity will over-estimate the stiffness and underestimate the warp propensity of the recovered lumber which contains a large amount of juvenile wood. FIGS. 1 and 2 illustrate the growth rate effect on measurement of stress wave velocity versus actual stiffness of lumber derived from a log via a cant (i.e. the stress wave velocity estimation problems associated with logs and trees). In addition to the diverse site and genetic factors, plantation stands have different silvicultural prescriptions during their long rotation. Thus, although the diameter, or the age, or both, of pre-harvest stands may be the same, the growth ring patterns of the trees could be very different. Previous studies have taught mathematical corrections for both diameter and SWV for the evaluation of MOE of logs. However, these corrections do not compensate for the impact of a percentage of juvenile wood in a sample.

It is known that stiffness is the one of the most deficient properties for structure wood products, and straightness is one of the most important factors in a lumber buying decision for builders. Therefore, stiffness and warp propensity are important properties of trees and logs used to manufacture wood products. Stiffness and warp propensity varies significantly within and between forest stands, and this offers an opportunity to rank and sort the trees and stands for genetic improvement and for allocating a particular material to the appropriate manufacturer to optimize the value through the forest cycle. Visual characteristics such as size and morphology of crown, stem, and branches may offer some indications of wood properties; however, trees or stands with identical morphologies often have very different stiffness and warp propensity levels. Rapid, nondestructive methods have been applied to sort and rank internal wood properties such as stiffness and warp propensity of trees, logs, stems or forest stands. However, these methods often cannot predict or rank MOE or warp propensity sufficiently because they do not compensate for growth rate differences.

A need, therefore, exists for a method for adjusting property calculations based on stress wave velocity measurements to compensate for growth rate differences amongst timber-based raw material groups.

BRIEF DESCRIPTION OF THE DRAWINGS

The embodiments of the present invention are described in detail below with reference to the following drawings.

FIG. 3 is a chart of data taken in a study of logs and lumber;

DETAILED DESCRIPTION OF THE INVENTION

Figure 2:
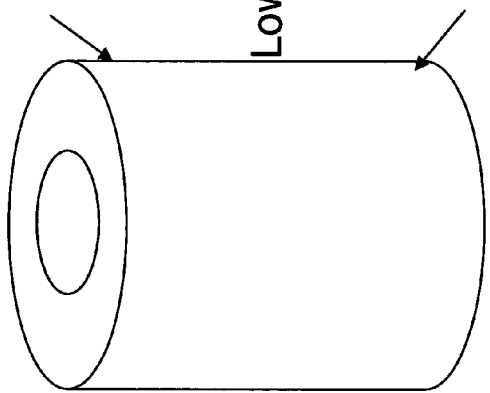
FIG. 2 is a perspective view of a log or tree having a high percentage of mature wood and the corresponding cant which may be derived from the log or tree.
Figure 1:
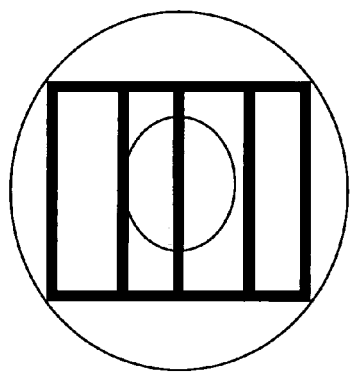
FIG. 1 is a perspective view of a log or tree having a low percentage of mature wood and the corresponding cant which may be derived from the log or tree.
Figure 1:
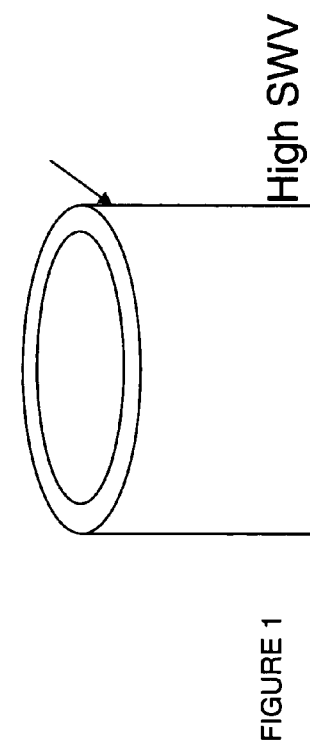
Figure 1:
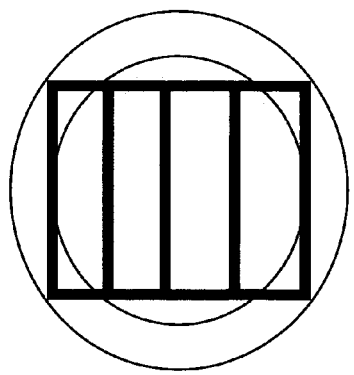

The present invention relates to methods for predicting properties based on stress wave velocity measurements, such as modulus of elasticity and/or warp potential of trees and/or logs and/or stems, for a timber-based raw material group. The term "timber-based raw material group" ("TBRMG") may be interpreted to encompass, for example, stands of timber, individual stems, collections of individual stems, individual logs, groups of logs, or the like. The methods provide a formula allowing compensation for growth rate differences between TBRMGs. Accordingly, the present invention prevents underestimation or overestimation of MOE and/or warp potential.

The present invention may be practiced using known tools for determining stress wave velocity within a wood product or specimen, such as a standing tree, log, board, or the like. In an embodiment, the stress wave velocity is measured at the cambium layer. Among these devices may be a FAKOPP® or a Director ST300® device. These types of devices involve the use of a first probe placed at a first location along a wood product and a second probe placed at a second location along the wood product. The first probe senses the initial pulse created by contact with the wood product, or other methods of stress wave inducement into the wood product. The second probe senses the pulse at the second location. This is commonly referred to as a "pitch-and-catch", or single pass, measurement. For standing trees, the pitch-and-catch method is one of the most commonly practiced methods due to the lack of a well-defined boundary of a standing tree.

Other devices which may be utilized in the practice of the present invention are, for example, devices such as a diameter tape or a caliper for determining log and/or tree diameter. In addition, devices such a Resistograph® or a Sibtec DmP (Digital microProbe) which detect decay and/or record the drilling depth and the crossing of high resistance latewood bands while drilling to determine ring patterns may be utilized. It is also contemplated that, in other embodiments, stress wave velocity may be determined via the use of resonance frequency. Methods and systems for making these types of determinations are known to those skilled in the art, such as for example, the HITMAN® or HM 200, and other resonance frequency measuring devices.

The present invention requires a determination or estimation of the amount of juvenile wood (the first 10-15 rings) within a tree, log, stem, or the like. This may be estimated by the percentage of stem's cross sectional area that is comprised of the first 10-15 rings.

It is generally known that stress wave velocity, also referred to as acoustic velocity, increases with ring age. Velocity that is measured using a standing tree stress-wave tool corresponds to travel of the wave through/across the rings that occupy approximately the outer 1-3 centimeters of growth. This outerwood acoustic velocity correlates well with MOE for stands of the same age provided that the numbers of rings in that outer zone are more or less the same, such as, for example, a "typical" southern pine plantation stand which is managed to produce relatively uniform ring spacing through its cycle. A reasonably accurate relationship between a FAKOPP reading and the MOE of a stand can be expected for all "typical" stands of the same age. However, a Fakopp/MOE relationship (or, MOE calculation based on FAKOPP measurements) developed for this typical stand will overestimate the MOE of a tree whose outer growth has stagnated and will underestimate the MOE of a tree with enhanced outer growth.

In an embodiment of the present invention, a method has been formulated for adjusting the measured stress wave velocity for a stand and, thereby, the calculated MOE. It is appreciated that the formula below is an example of an embodiment and that the term "TBRMG" could be substituted for the term "Stand" in the formula to encompass for example, stands of timber, individual stems, collections of individual stems, individual logs, groups of logs, or the like. The method includes the formula below:

$$\text{Stand } MOE = K_1 + K_2 * SWV_{Test\ Stand} + K_3 * JW_c$$

Where:

$K1$ is the intercept and $K2$ and $K_3$ are regression coefficients of the regression equation.

$SWV_{Test\ Stand}$=Average stress wave velocity (unit=meter per second) of the stand being tested (average of standing tree stress wave velocities taken at breast height using a FAKOPP or similar device)

$JW_c$=The difference between the percentage of juvenile wood of the stand currently being tested and the average percentage of the juvenile wood of all the stands being compared (% $JW_{Average}$-% $JW_{Test\ Stand}$).

The regression equation is determined using least squares estimation. The regression determination involves performing a regression determination utilizing modulus of elasticity as a dependent variable, and stress wave velocity and $JW_c$ as independent variables.

Stand average diameter at the breast height, or "DBH" recorded in inventory data at the time of an age 10-15 silviculture operation such as thinning can be used as the juvenile core diameter to estimate the percentage of juvenile wood. The percentage of juvenile wood is equal to 100* (thinning diameter^2/Log diameter ^2). The correction factor JWc is the difference between the percentage of juvenile wood of an individual stand and the mean of the population of the stands being compared. Although % $JW_{Test\ Stand}$ can be used directly in the regression to improve MOE prediction, the use of the term (% $JW_{Average}$-% $JW_{Test\ Stand}$) provides additional information on overestimation or underestimation of an individual stand. For example, a stand with fast early growth and stagnant late growth (tight outer rings) yields a time-of-flight SWV measurement that overestimates the average MOE of lumber recovered form the center cant. Such a stand has a high percentage of juvenile wood or a negative value for $JW_c$, which reduces the effects of the overestimation.

An advantage of the present invention is that the parameters % $JW_{Test\ Stand}$ and % $JW_{Average}$ can be estimated from inventory records if that data includes reliable diameter data (or estimates) at various ages. Alternatively, those parameters can be estimated using increment cores or arborist tools, such as a Sibtec DmP or a Resistograph®, or other devices which measure ringwidth pattern or wood decay. Those parameters also can be measured directly from log ends.

A similar equation may apply for determination of warp potential. For example, MOE can be replaced by lumber crook in the equation. It is understood that the term crook is used in the embodiment described below; however, other forms of warp, such as bow, twist, cup, or the like may be substituted in the equation below in a manner known to those skilled in the art. Further, it is appreciated that the formula below is an example of an embodiment and that the term "TBRMG" could be substituted for the term "Stand" in the formula to encompass for example, stands of timber, individual stems, collections of individual stems, individual logs, groups of logs, or the like. A large magnitude of adjustment may be necessary, for example (% $JW_{Average}$-% $JW_{Test\ Stand})^3$, for warp prediction because the impact of a steep shrinkage gradient of juvenile wood on warp is stronger than that on MOE. The formula may then appear as follows:

$$\text{Lumber Crook} = K_1 + K_2 * SWV_{Test\ Stand} + K_3 * JW_c$$

Where:

$K1$ is the intercept and $K2$ $K_3$ are regression coefficients of the regression equation.

$SWV_{Test\ Stand}$=Average stress wave velocity of the stand being tested (average of standing tree stress wave velocities taken at breast height using a FAKOPP or similar device).

$JW_c$=Cube of the difference between the percentage of juvenile wood of the stand currently being tested and the average percentage of juvenile wood of all the stands being compared (% $JW_{Average}$-% $JW_{Test\ Stand})^3$. (% JW=100× (Diameter of the stand at age 10-15 years)$^2$÷(Diameter of the stand at current age)$^2$.

The regression equation is determined using least squares estimation. The regression determination involves performing a regression determination utilizing warp potential as a dependent variable, and stress wave velocity and $JW_c$ as independent variables.

In an embodiment, the method may be performed via the following steps. In a first step, a number of trees within a TBRMG may be measured for stress wave velocity via any of the known methods mentioned above and readily understood by those skilled in the art. This may provide a value which is representative of the TBRMG. In an alternate embodiment, the trees may be felled and the resulting logs may be examined for stress wave velocity. In an example, a butt log portion is examined. In a following step, the percentage of juvenile wood may be determined and/or estimated. In a first step, tree diameters at breast height at age 10-15 juvenile diameter) and at harvest age (log diameter) can be estimated from inventory records. Alternatively, these diameters can be measured on standing trees using increment cores or arborist tools, such as a Sibtec DmP or a Resistograph®, or other devices which measure ringwidth pattern or wood decay. In an alternate embodiment, these diameters can be measured directly from the end of a stem or from the ends of a log. Percent juvenile wood of a tree or a log can be calculated as 100 times the ratio of the square of the juvenile diameter and the square of the log diameter. The average percentage of juvenile wood of the sampled trees or logs of the test TBRMG is the $JW_{Test\ TBRMG}$, and the average of juvenile wood measured for all TBRMGs is the $JW_{Average}$. The adjustment variable, JWc, is % $JW_{Average}$-% $JW_{Test\ TBRMG}$.

The following example provides an embodiment of the present invention, but should not be considered to be entirely representative with respect to steps such as velocity measuring, ring pattern determination, or related steps:

EXAMPLE 1

Figure 4:
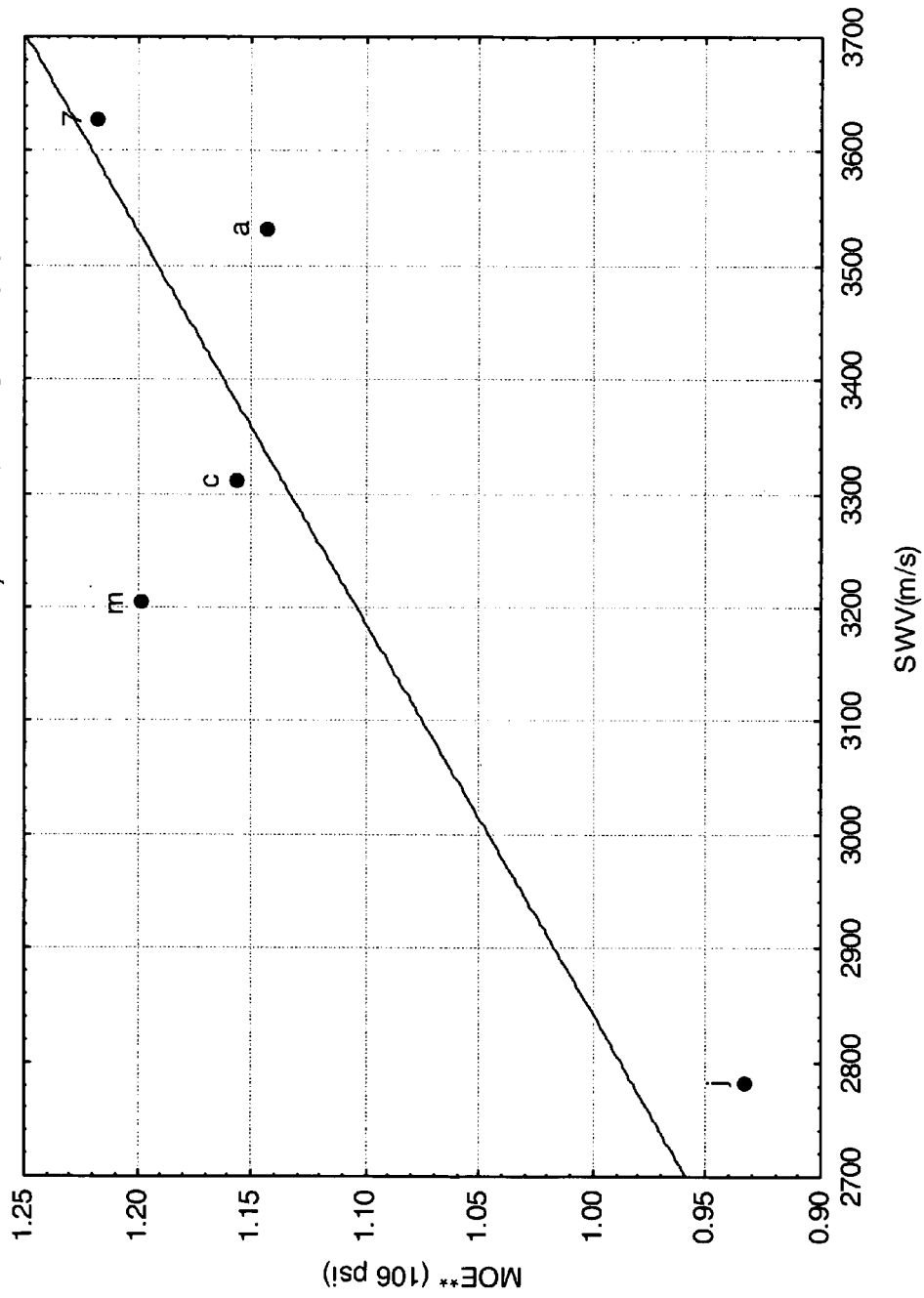
FIG. 4 is a plot of modulus of elasticity ("MOE") versus measured stress wave velocity for the stands listed in the chart of FIG. 3.
Figure 5:
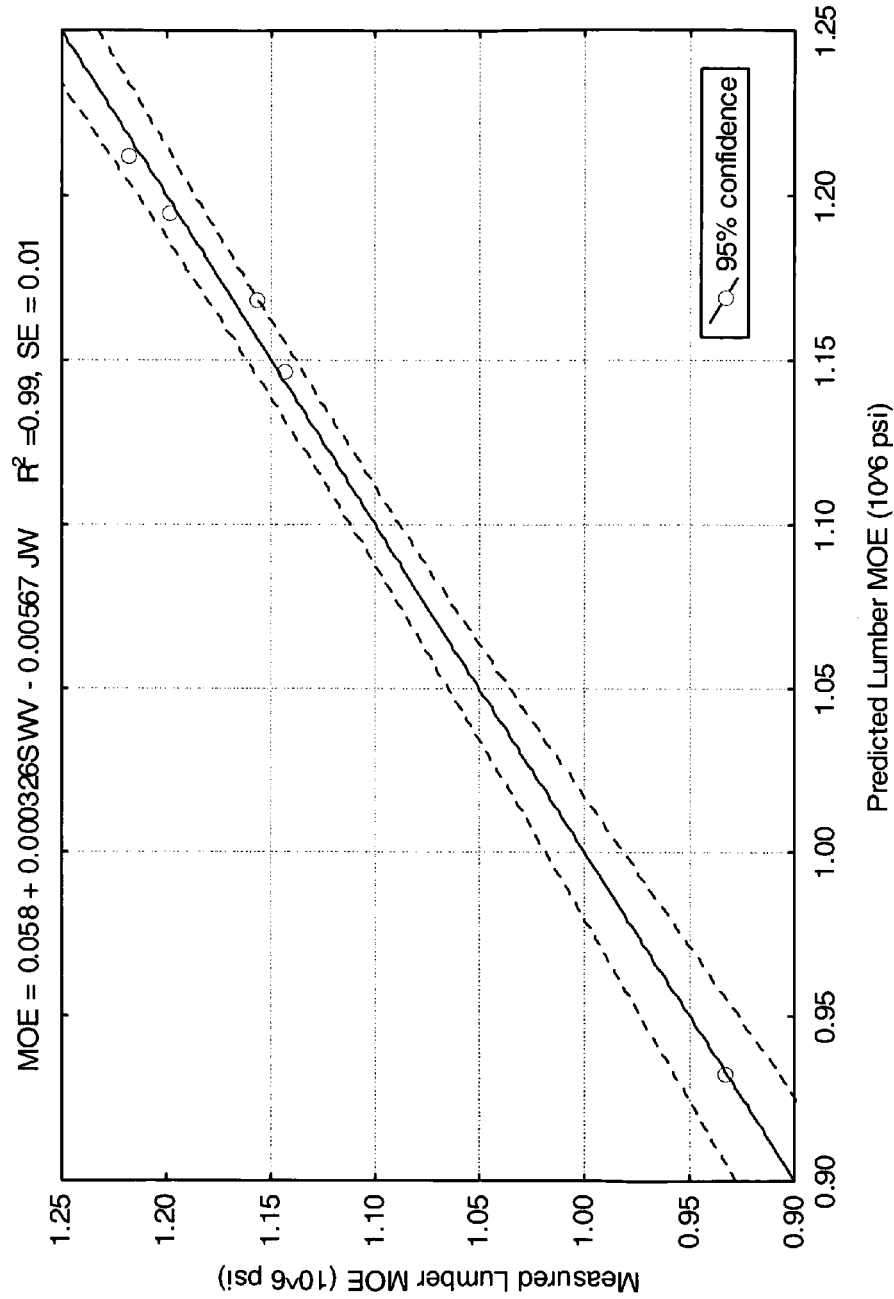
FIG. 5 is a plot of measured modulus of elasticity versus predicted modulus of elasticity in which the data has been adjusted using the method of the present invention.
Figure 6:
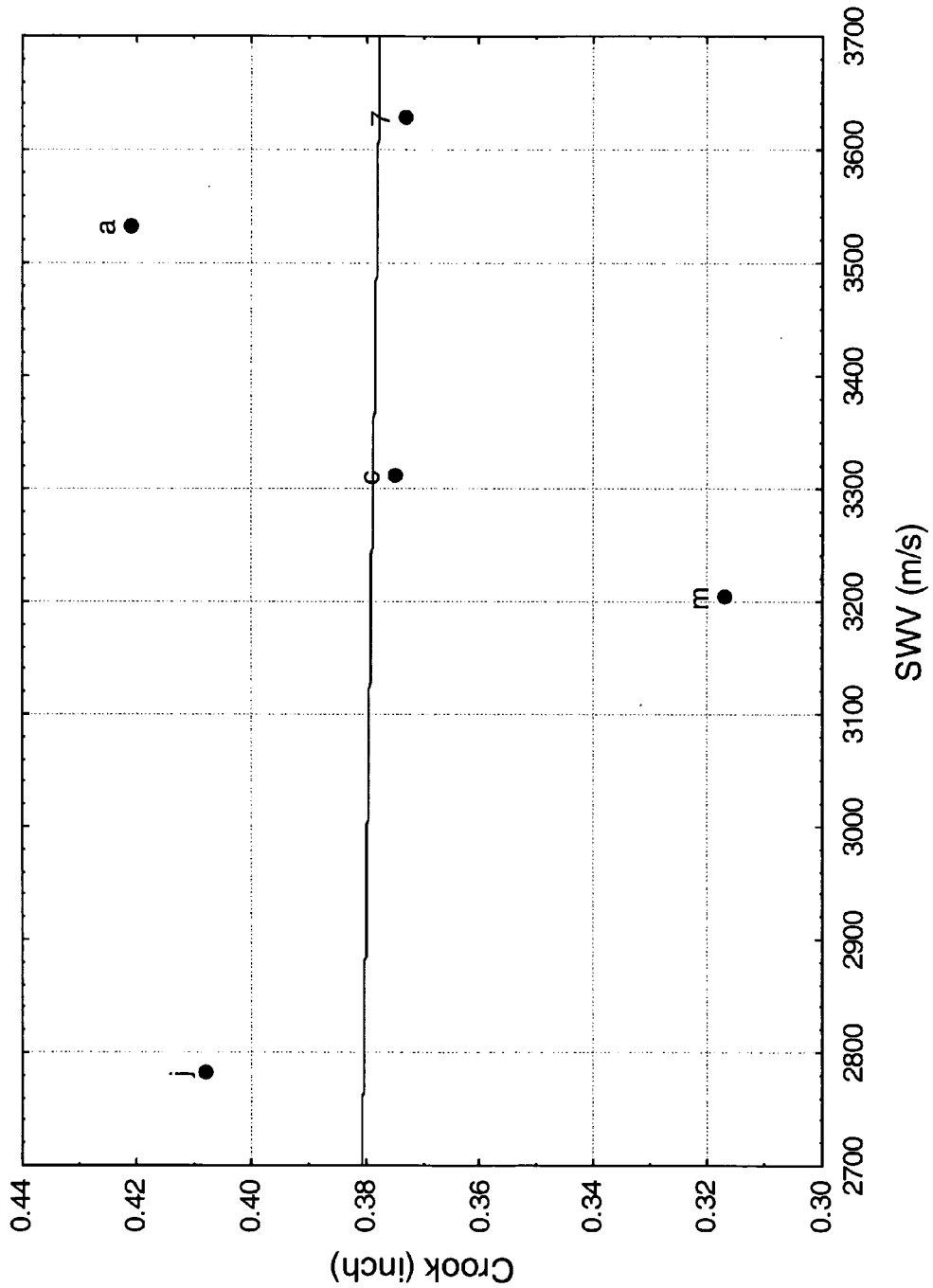
FIG. 6 is a plot of crook versus measured stress wave velocity for the stands listed in the chart of FIG. 3.
Figure 7:
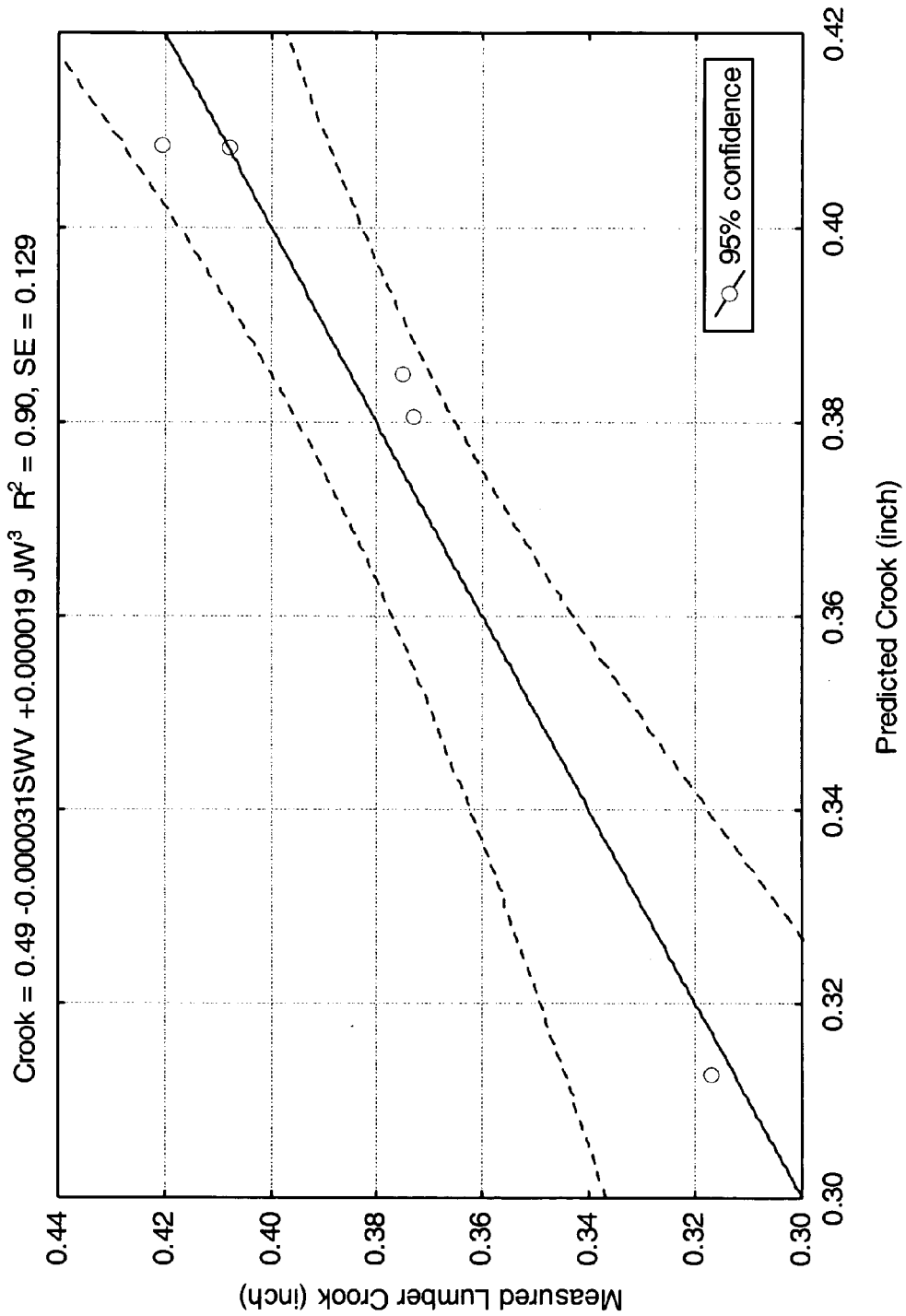
FIG. 7 is a plot of measured crook versus predicted crook in which the data has been adjusted using the method of the present invention.

A study conducted in 1996 at a mill owned by Weyerhaeuser Company examined five pruned stands of 26 year old loblolly pines. The results are illustrated in FIG. 3. The specimens had similar tree diameter at breast height ("DBH"). The DBH ranged from 13 inches to 15 inches, with an average of 14 inches. Standing tree stress wave velocity was measured on 25 trees per stand. The logs were processed and tracked through the mill. Average lumber MOE and average crook of the recovered lumber of the stands were measured. Average lumber MOE versus stress wave velocity is illustrated in FIG. 4. As shown in the plot, actual MOE of stands m and a are over or under the values predicted by SWV measurement. FIG. 5 illustrates a plot of predicted versus measured MOE after adjustment of the data via the formula outlined above. As shown in the plot, the standard error has decreased (0.07 versus 0.01). This indicates an increased accuracy of approximately 86%. Average lumber crook versus stress wave velocity is illustrated in FIG. 6. No relationship between lumber crook and SWV was found according to the results. However, FIG. 7 illustrates a plot of predicted versus measured crook after adjustment of the data via the formula outlined above. As shown in the plot, lumber crook can be reasonably predicted after the adjustment. The results of the example demonstrated that using SWV alone to predict and to rank MOE or warp propensity of timber-based raw material groups may not be sufficient. A correction on the percentage of juvenile wood is necessary to improve the accuracy and the predictions and to obtain a correct ranking.

While the embodiments of the invention have been illustrated and described, as noted above, many changes can be made without departing from the spirit and scope of the invention. Accordingly, the scope of the invention is not limited by the disclosure of the embodiments. Instead, the invention should be determined entirely by reference to the claims that follow.

What is claimed is:

1. A method for sorting a timber-based raw material group, the method comprising the steps of:
    obtaining a stress wave velocity which is representative for each of a first, second and third timber-based raw material group (hereinafter referred to as "TBRMG");
    obtaining an average diameter for each of the first, second and third TBRMG;
    obtaining an average diameter of juvenile wood for each of the first, second and third TBRMG;
    obtaining measured modulus of elasticity data for the first, second and third TBRMG;
    determining a percentage of juvenile wood for each of the first, second and third TBRMG;
    obtaining a correction factor $JW_c$ for any of the first, second, or third TBRMG which is equal to a difference between an average percentage of juvenile wood for the first, second and third TBRMG, and a percentage of juvenile wood for any of the first, second or third TBRMG, respectively;
    performing a regression determination utilizing modulus of elasticity as a dependent variable, and stress wave velocity and $JW_c$ as independent variables;
    predicting modulus of elasticity of the particular TBRMG from the equation:

$$TBRMG\ MOE = K_1 + K_2 * SWV_{Test\ TBRMG} + K_3 * JW_c$$

Where:
    K1 is the intercept and K2 and $K_3$ are regression coefficients of the regression equation;
    $SWV_{Test\ TBRMG}$=Average stress wave velocity of the TBRMG being tested; and
    $JW_c$=The difference between the percentage of juvenile wood of the TBRMG currently being tested and the average percentage of the juvenile wood of all the TBRMGs being compared (% $JW_{Average}$-% $JW_{Test\ TBRMG}$); and
    sorting the particular TBRMG based on the predicted modulus of elasticity.

2. The method of claim 1 wherein the stress wave velocity is based on an acoustic velocity measurement taken near a cambium layer of one or more trees or logs within the TBRMG.

3. The method of claim 1 wherein the determination of juvenile wood is based on measurement of growth ring patterns at one or more cross sections.

4. The method of claim 1 wherein the determination of juvenile wood is based on examination of an extracted increment core.

5. The method of claim 1 wherein the determination of juvenile wood is performed by a device which measures ringwidth pattern or wood decay.

6. The method of claim 1 wherein the stress wave velocity is based on an ultrasonic velocity measurement taken near a cambium layer of one or more trees or logs within the TBRMG.

7. The method of claim 1 wherein the determination of juvenile wood is based on TBRMG growth records.

8. A method for sorting a timber-based raw material, the method comprising the steps of:

obtaining a stress wave velocity which is representative for each of a first, second and third TBRMG;

obtaining an average diameter for each of the first, second and third TBRMG;

obtaining an average diameter of juvenile wood for each of the first, second and third TBRMG;

obtaining measured warp data for the first, second and third TBRMG;

determining a percentage of juvenile wood for each of the first, second and third TBRMG;

obtaining a correction factor $JW_c$ for any of the first, second, or third TBRMG which is equal to the cube of a difference between an average percentage of juvenile wood for the first, second and third TBRMG, and a percentage of juvenile wood for any of the first, second or third TBRMG, respectively;

performing a regression determination utilizing warp potential as a dependent variable, and stress wave velocity and $JW_c$ as independent variables; and predicting warp potential of the particular TBRMG from the equation:

Warp Potential=$K_1+K_2*SWV_{Test\ TBRMG}+K_3*JW_c$

Where:

K1 is the intercept and K2 and $K_3$ are regression coefficients of the regression equation;

$SWV_{Test\ TBRMG}$=Average stress wave velocity of the TBRMG being tested;

$JW_c$=Cube of the difference between the percentage of juvenile wood of the TBRMG currently being tested and the average percentage of juvenile wood of all the TBRMGs being compared (% $JW_{Average}$−% $JW_{Test\ TBRMG}$)$^3$; and sorting the particular TBRMG based on the predicted warp potential.

9. The method of claim 8 wherein the warp is in the form of crook.

10. The method of claim 8 wherein the warp is in the form of bow.

11. The method claim 8 wherein the warp is in the form of twist.

12. The method of claim 8 wherein the warp is in the form of cup.

13. The method of claim 8 wherein the stress wave velocity is based on an acoustic velocity measurement taken near a cambium layer of one or more trees or logs within the TBRMG.

14. The method of claim 8 wherein the determination of juvenile wood is based on measurement of growth ring patterns at one or more cross sections.

15. The method of claim 8 wherein the determination of juvenile wood is based on examination of an extracted increment core.

16. The method of claim 8 wherein the determination of juvenile wood is performed by a device which measures ringwidth pattern or wood decay.

17. The method of claim 8 wherein the stress wave velocity is based on an ultrasonic velocity measurement taken near a cambium layer of one or more trees or logs within the TBRMG.

18. The method of claim 8 wherein the determination of juvenile wood is based on TBRMG growth records.

* * * * *